United States Patent [19]

Drews

[11] Patent Number: 5,180,390
[45] Date of Patent: Jan. 19, 1993

[54] INTRAOCULAR LENS WITH REINFORCING ELEMENT

[76] Inventor: Robert C. Drews, 211 N. Meramec Ave., Clayton, Mo. 63105

[21] Appl. No.: 738,093

[22] Filed: Jul. 30, 1991

[51] Int. Cl.⁵ .............................................. A61F 2/16
[52] U.S. Cl. ............................................................ 623/6
[58] Field of Search ............................................... 623/6

[56] References Cited

U.S. PATENT DOCUMENTS

| | | | |
|---|---|---|---|
| 4,424,597 | 1/1984 | Schlegel | 623/6 |
| 4,615,702 | 10/1986 | Koziol et al. | 623/6 |
| 4,666,445 | 5/1987 | Tillay | 623/6 |
| 4,846,832 | 7/1989 | Wichterle | 623/6 |

FOREIGN PATENT DOCUMENTS

| | | | |
|---|---|---|---|
| 2124500A | 2/1984 | United Kingdom | 623/6 |
| WO90/01306 | 2/1990 | World Int. Prop. O. | 623/6 |

*Primary Examiner*—Ronald Frinks
*Attorney, Agent, or Firm*—Hugh D. Jaeger

[57] ABSTRACT

An intraocular lens with an optic of a polymer material and a skirt of polymer material with a reinforcing element used in, about or on the periphery of the skirt of the intraocular lens. In one specific embodiment, a reinforcing element is positioned in the outer circumference of a flexible skirt which supports the optic. The skirt can be folded about the optic so that the lens can be inserted through a minimal incision. In another embodiment, the skirt can be rectangular. The outer loop can either attach to the optic or be integral to the edge of the optic. In an additional embodiment, the reinforcing element can be attached about the edge of the skirt.

3 Claims, 5 Drawing Sheets ically pertains to an integral intraocular lens including a thin, flexible skirt surrounding an optic with a stiffener member such as a polymer or stainless steel embedded in the outer periphery of the flexible skirt for reinforcement of the skirt.

2. Description of the Prior Art

Prior art soft material intraocular lenses, while flexible in nature, have not included a reinforcing element about or in the lens for placement in the eye, and for positioning and stiffening of an edge of the lens. Currently, soft lenses which are made of silicone or HEMA, which need a certain amount of stiffening, requiring a large or heavy skirt or haptic to support the lens in the eye.

The present invention overcomes the disadvantages of the prior art by providing an intraocular lens with a loop of reinforcing material about or in a thin flexible skirt of the lens providing support.

SUMMARY OF THE INVENTION

The general purpose of the present invention is to provide an intraocular lens with a thin flexible skirt and with a reinforcing element for a stiff edge which is still flexible. The lens can include a planar skirt or a vaulted skirt.

According to one embodiment of the present invention, there is provided an intraocular lens including a central optic, and a thin member extending outwardly from the central optic to the outer periphery of the lens. A filament-like member, such as loop material, is embedded in or about a flexible skirt peripheral edge to provide a degree of support and stiffness to the overall lens, while still having sufficient flexibility for the bending and folding of the flexible skirt during ocular insertion. This provides that a minimal incision can be utilized.

According to another embodiment of the present invention, there is provided an intraocular lens with an optic, a skirt surrounding the optic, and a reinforcing element in the edge of the skirt. The optic, for example, could be 5 mm wide, but the optic could be round, oval or any other shape. The haptic skirt and reinforcing element can be of the same material or of different materials. There are other reinforcing loop configurations, such as separate reinforced loops into the optic, or in the alternative a continuous loop around the optic, and the loop can be of any geometrical configuration.

Still another alternative embodiment of the present invention provides a skirted lens within the teachings of the present invention including a flexible and foldable central optic member with a reinforced skirt wherein the entire intraocular lens is folded about the central optic.

Significant aspects and features of the present invention include an intraocular lens with a very thin, flexible skirt with a stiff edge which is still flexible. This therefore results in a very light intraocular lens with a minimal, and more foldable cross-sectional area. The skirt can be either a planar configuration or a vaulted configuration.

One significant aspect and feature of the present invention is an intraocular lens having a flexible and bendable skirt surrounding the central optic.

Another significant aspect and feature of the present invention is a peripheral member embedded in or about the outer periphery of the flexible lens skirt providing for support of the optic and the skirt.

Another significant aspect and feature of the present invention is a skirted lens having a flexible or rigid optic and a flexible reinforced skirt which is highly flexible for intraocular insertion.

Another significant aspect and feature of the present invention is a reinforcement within or about the periphery of the skirt which insures that the skirt will resume an optimum position and predetermined geometrical shape once the lens has been placed in the eye.

Having thus described embodiments of the present invention, it is the principal object hereof to provide an intraocular lens with a reinforcing element or a stiffening element embedded about the optic or a support for the optic, or into the optic.

An object of the present invention is to provide a lightweight, thin intraocular lens of a material with memory, which is flexible for insertion, and includes a reinforced edge or skirt which reserves and maintains a predetermined desired geometrical configuration after implantation.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

Figure 1:
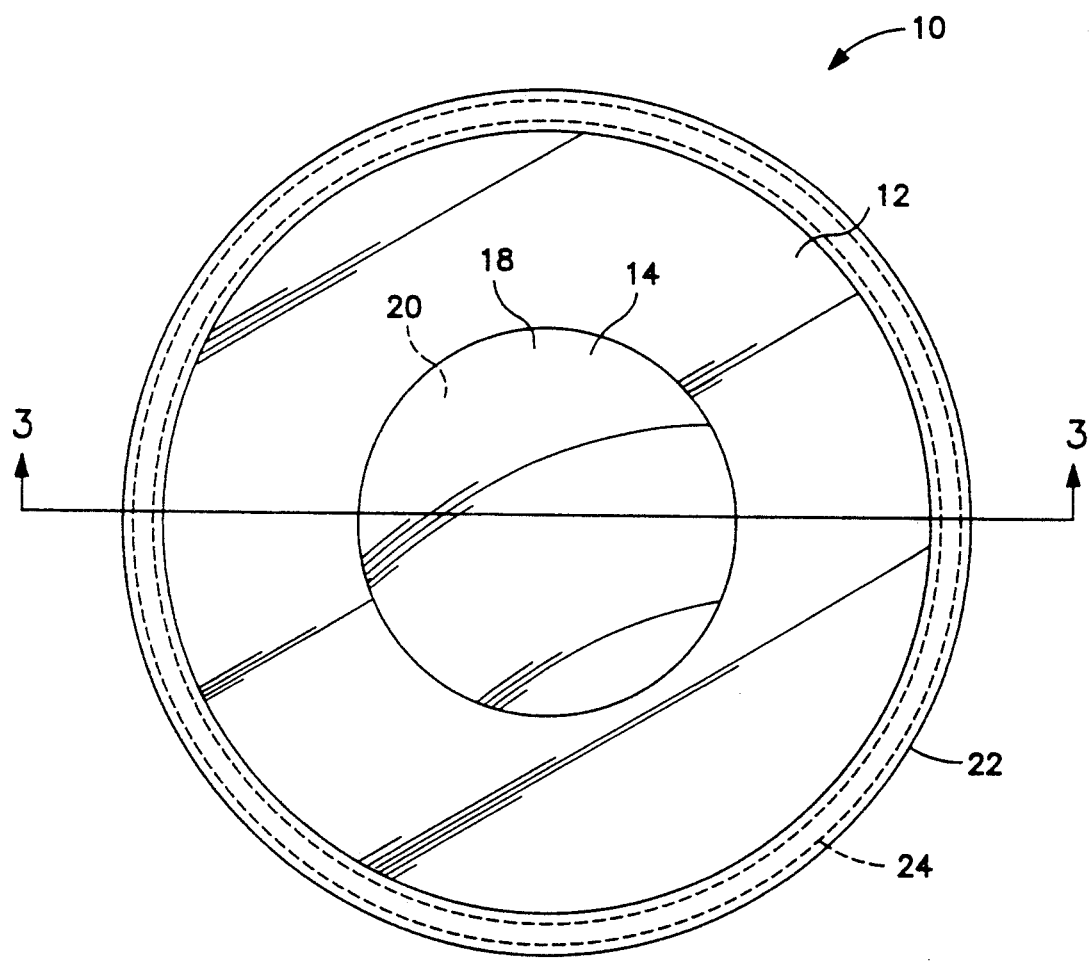
FIG. 1 illustrates a plan view of an intraocular lens with a reinforced skirt.

10 lens
12 thin planar skirt member
14 central optic
16 integral edge
18 anterior surface 20 posterior surface
22 integral edge
24 stiffener member
30 intraocular lens
32 central optic
34 anterior surface
36 posterior surface
38 loop
40 loop
42 hole
44 hole
46 hole
48 hole
50 lens edge
52 thin planar skirt member
54 thin planar skirt member
56 edge
58 edge
60 intraocular lens
62 central optic
64 anterior surface
66 posterior surface
68 stiffener loop
70 edge
72 thin planar skirt member
74 thin planar skirt member
76 continuous edge
100 lens
112 skirt member
114 central optic
118 anterior surface
120 posterior surface
122 edge
124 stiffener member
150 intraocular lens
152 central optic
154 anterior surface
156 posterior surface
158 flexible skirt member
160 flexible polymer arcular stiffener member

DESCRIPTION OF THE PREFERRED EMBODIMENTS

Figure 2:
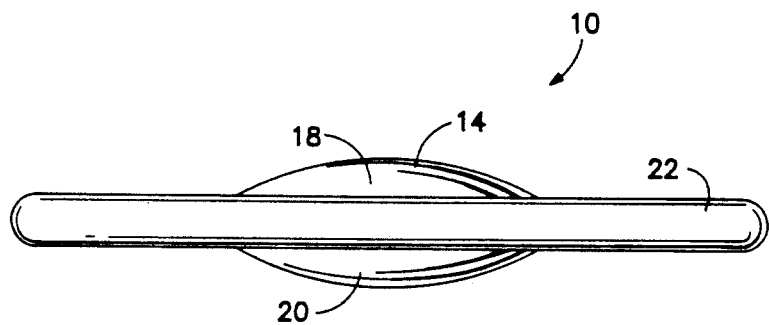
FIG. 2 illustrates a side view of the present invention.

FIG. 1 illustrates a plan view of an intraocular lens 10. A flexible thin planar skirt member 12 extends outwardly from a round shaped central optic 14 and intersects with a flexible integral edge 22. The central optic 14 includes an anterior surface 18 and a posterior surface 20. The edge 22 has a round or otherwise thickened cross section and includes an embedded flexible polymer arcular stiffener member 24, such as a ring of flexible PMMA, polypropylene or other like suitable polymer material. The arcular stiffener member 24 can also have an oval, square, semicircular or any other cross section as desired. The skirt member 12 and the edge 22 are flexible enough so that the structures can be sufficiently folded or bent for ocular insertion. The profile of the lens 10 is planar as illustrated in FIG. 2; however, the skirt 12, the edge 22 and the stiffener member can be angled forward or backward in a cone like fashion out of the plane of the lens or can even be curved forward or backward out of the plane of the lens. While a conical configuration is not specifically illustrated in the figures, a conical configuration is within the teachings of the present invention. When folded, the lens 10 offers a minimal cross-sectional area through a small incision. The lens optic can be of any suitable material, such as a polymer, PMMA, silicone or HEMA. The optic can be either hard or soft as a physical property. The skirt can be of any suitable material, such as a polymer, silicone, HEMA, a flexible PMMA, polypropylene, DACRON (polyethylene terephlhatate), of polyurethane. In the alternative, the edge 22 and/or the skirt 12 can also be opaque such as the color black or blue to preclude stray light from being transmitted from the edge 22 and/or through the planar skirt 12 member to interfere with the central optic 14 or the eye. The optic, skirt or reinforcing element can be made of any other suitable materials which are compatible with the eye. The lens optic can assume any optical configuration, such as biconvex, meniscus, or plano-convex. The optic and skirt can be of the same material and formed as a continuous integral member and the reinforcing element formed into or about the edge of the skirt.

FIG. 2 illustrates a side view of FIG. 1 where all numerals correspond to those elements previously described.

Figure 3:
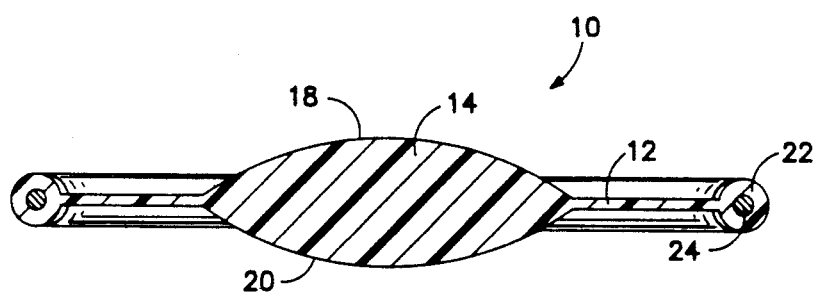
FIG. 3 illustrates a cross-sectional view along line 3—3 of FIG. 1.

FIG. 3 illustrates a cross-sectional view along line 3—3 of FIG. 1 where all numerals correspond to those elements previously described.

MODE OF OPERATION

The thin planar skirt member 12, the integral edge 22 and the reinforcing or stiffener element or member 24 of the lens 10 can be bent about the central optic 14 for passage of the intraocular lens through a small incision. Further, the material for the reinforcing element or stiffener member 24 maintains a memory to return to the original optic and geometrical position for subsequent positioning within the chamber of the eye. Alternately, the skirt 12 and the stiffener member 24 may be angled or curved forward or backward from the plane of the lens optic 20 to provide vaulting as desired.

DESCRIPTION OF THE FIRST ALTERNATIVE EMBODIMENT

Figure 4:
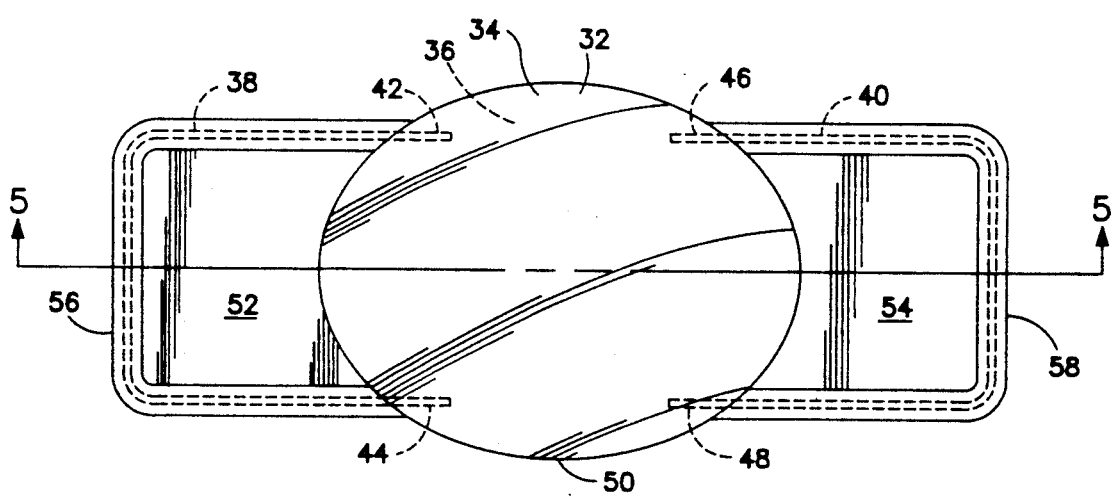
FIG. 4 illustrates a plan view of a first alternative embodiment of an intraocular lens.

FIG. 4 illustrates a plan view of a first alternative embodiment 30 of the present invention where separate loops extend into the optic for supporting the lens. In this particular example and for purposes of illustration only and not to be construed as limiting of the present invention, there is provided an oval optic of suitable material. The optic could also be round. The intraocular lens 30 includes a central optic 32 with an anterior surface 34 and a posterior surface 36. Polymer stiffener or support loops 38 and 40, such as flexible polypropylene, PMMA, or other like suitable polymer material, secure into holes 42, 44, 46 and 48 in the lens edge 50, such as by frictional engagement, welding, adhesive or other suitable means. Thin planar skirt members 52 and 54 extend from the lens edge 50 between the holes 42–44 and 46–48 and the loop members 38 and 40, respectively. The thin planar skirt members 52 and 54 form around and about the loop members 38 and 40 to embed the loop members 38 and 40 and to form edges 56 and 58, each having a round cross section such as that illustrated in FIG. 5. Other cross-sections could be utilized. The skirt members 52 and 54 and the edges 56 and 58 are flexible enough so that the structures can be sufficiently folded for ocular insertion. When folded, the lens offers a minimal cross-sectional area through a small incision. The lens, skirt and loops retain memory to return to its original optical and geometrical shape.

Figure 5:
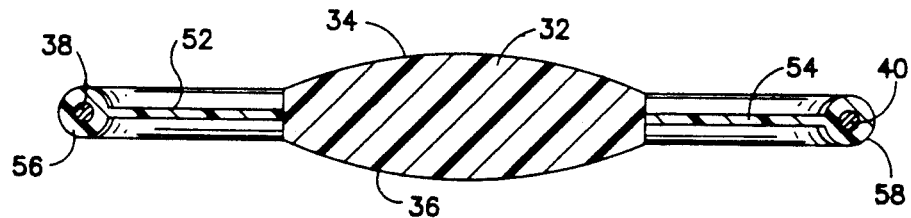
FIG. 5 illustrates a cross-sectional view along line 5—5 of FIG. 4.

FIG. 5 illustrates a cross-sectional view along line 5—5 of FIG. 4 where all numerals correspond to those elements previously described.

Alternatively, the skirt members 52 and 54 may be angled or curved ("vaulted") forward or backward out of the plane of the lens optic 32.

DESCRIPTION OF THE SECOND ALTERNATIVE EMBODIMENT

Figure 6:
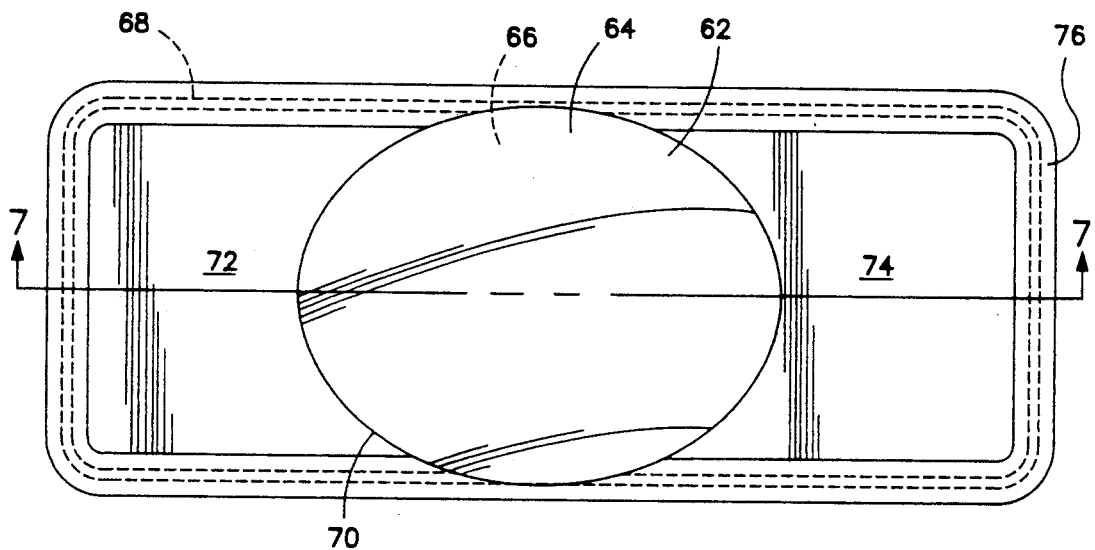
FIG. 6 illustrates a plan view of a second alternative embodiment of an intraocular lens.

FIG. 6 illustrates a plan view of a second alternative embodiment 60 of a continuous reinforced loop around an optic. In this particular example and for purposes of illustration only and not to be construed as limiting of the present invention, there is provided an oval optic of a polymer. The intraocular lens 60 includes a central optic 62 which is oval in shape. The central optic 62 includes an anterior surface 64 and a posterior surface 66. A continuous one piece polymer stiffener or support loop 68 in the form of a rectangle or other suitable geometric design such as polypropylene, PMMA, or other like suitable polymer material aligns secured in close proximity to the edge 70, or may align and secure to the optic edge, such as by medical adhesives, welding, gluing or other suitable securing processes. It is noted that the support loop 68 comes in close proximity to the central optic 62 whereas in FIG. 1 the support loop stiffening member 24 remains at a constant radius from the central optic 14. Thin planar skirt members 72 and 74 extend outwardly from the optic edge 70 to meet and intersect the continuous stiffener loop 68. The thin planar skirt members 72 and 74 form over and about the continuous loop stiffener member 68 to embed the stiffener member 68 and to form a continuous edge 76 having a round cross section, such as that illustrated in FIG. 7. The thickness of the skirt members 72 and 74 is further determined by the particular characteristics of the specific material and can be thicker or thinner than that degree of thickness illustrated in the figures. The skirt members 72 and 74 are flexible enough so that the structures can be sufficiently folded for ocular insertion. When folded, the lens offers a minimal cross-sectional area through a small incision such as the folded configurations of FIGS. 8 and 9.

Figure 7:
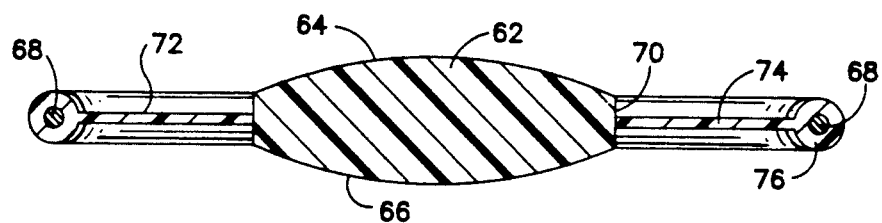
FIG. 7 illustrates a cross-sectional view taken along line 7—7 of FIG. 6.

FIG. 7 illustrates a cross-sectional view along line 7—7 of FIG. 6 where all numerals correspond to those elements previously described. Alternatively, the skirt and support members may be angled or curved ("vaulted") forward or backward out of the planes of the lens optic.

Figure 8:
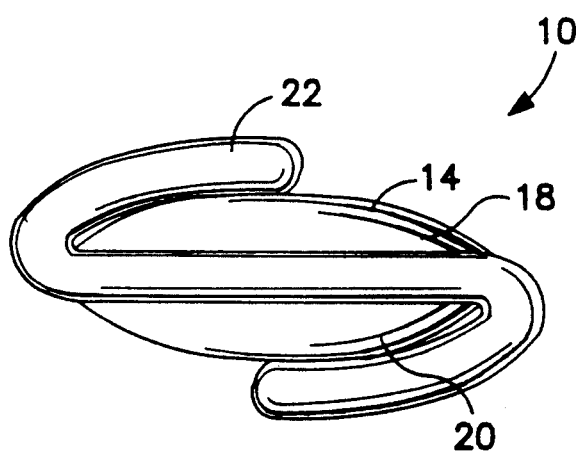
FIG. 8 illustrates a side view of the intraocular lens folded for insertion into an incision.

FIG. 8 illustrates a side view of an intraocular lens 10 folded for ocular insertion where all numerals correspond to those elements previously described. The left portion edge 22 is folded upwardly to lie over and about the anterior surface 18 and the right portion of the edge 22 is folded downwardly to lie over and about the posterior surface 20 to present a low profile folded lens for insertion into and through a small incision. Other like folding configurations are applicable to the teachings of the present invention as well as those folding configurations illustrated in the other illustrations.

Figure 9:
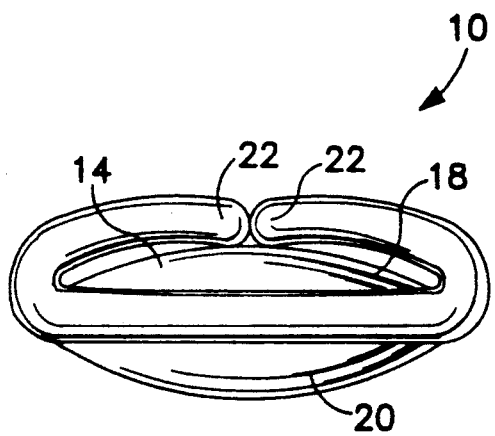
FIG. 9 illustrates a side view of the intraocular lens folded for insertion into one to many spaces in an incision.

FIG. 9 illustrates a side view of the intraocular lens 10 folded for ocular insertion where all numerals correspond to those elements previously described. The left portion of the edge 22 is folded up to lie over and about the anterior surface 18 and the right portion of the edge 22 is also folded upwardly to lie over and about the anterior surface 18 of the optic 14 to present a low profile folded lens for insertion into a small incision.

DESCRIPTION OF THE THIRD ALTERNATIVE EMBODIMENT

Figure 10:
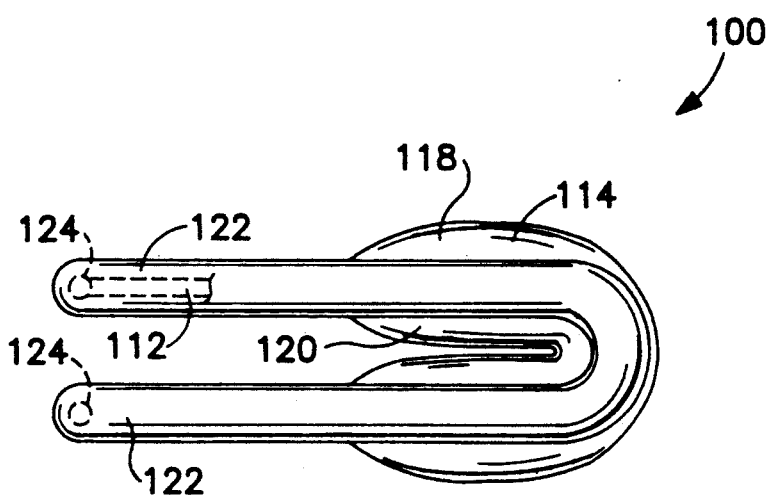
FIG. 10 illustrates a side view of a third alternative embodiment of an intraocular lens having a flexible optic folded for insertion into an incision.

FIG. 10, a third alternative embodiment, illustrates a side view of an intraocular lens 100 with a flexible optic folded for ocular insertion where all numerals correspond to those elements previously described. The intraocular lens 100 is similar to the lens 10 described in FIG. 1 except that the central optic 114 is flexible. The intraocular lens 100 includes the central optic 114 having an anterior surface 118, a posterior surface 120, an embedded polymer arcular stiffener member 124 embedded in an edge 122 and a skirt member 112. The method of folding the edges in this and previous figures are for purposes of illustration and not to be construed as limiting of the present invention. Other variations in folding of the edges of the intraocular lens may also be used and those illustrated shall not be construed to be limiting of the scope of the present invention. In this illustration, the entire intraocular lens 100 is folded where the fold occurs through the central optic 114, and where the edge 122 folds as well in folding alignment with the central optic 114 to align the edge 122 with itself in a parallel fashion as illustrated and may fold further to allow edge member 122 to contact itself to present a low profile folded lens for insertion into a small incision.

Optionally, the same method of folding of the edges 122, similar to the edge 22 as illustrated and described in FIGS. 8 and 9, can be incorporated over and about the flexible central optic 114 should the surgeon opt to not fold the flexible central optic 114 for insertion.

DESCRIPTION OF THE FOURTH ALTERNATIVE EMBODIMENT

Figure 11:
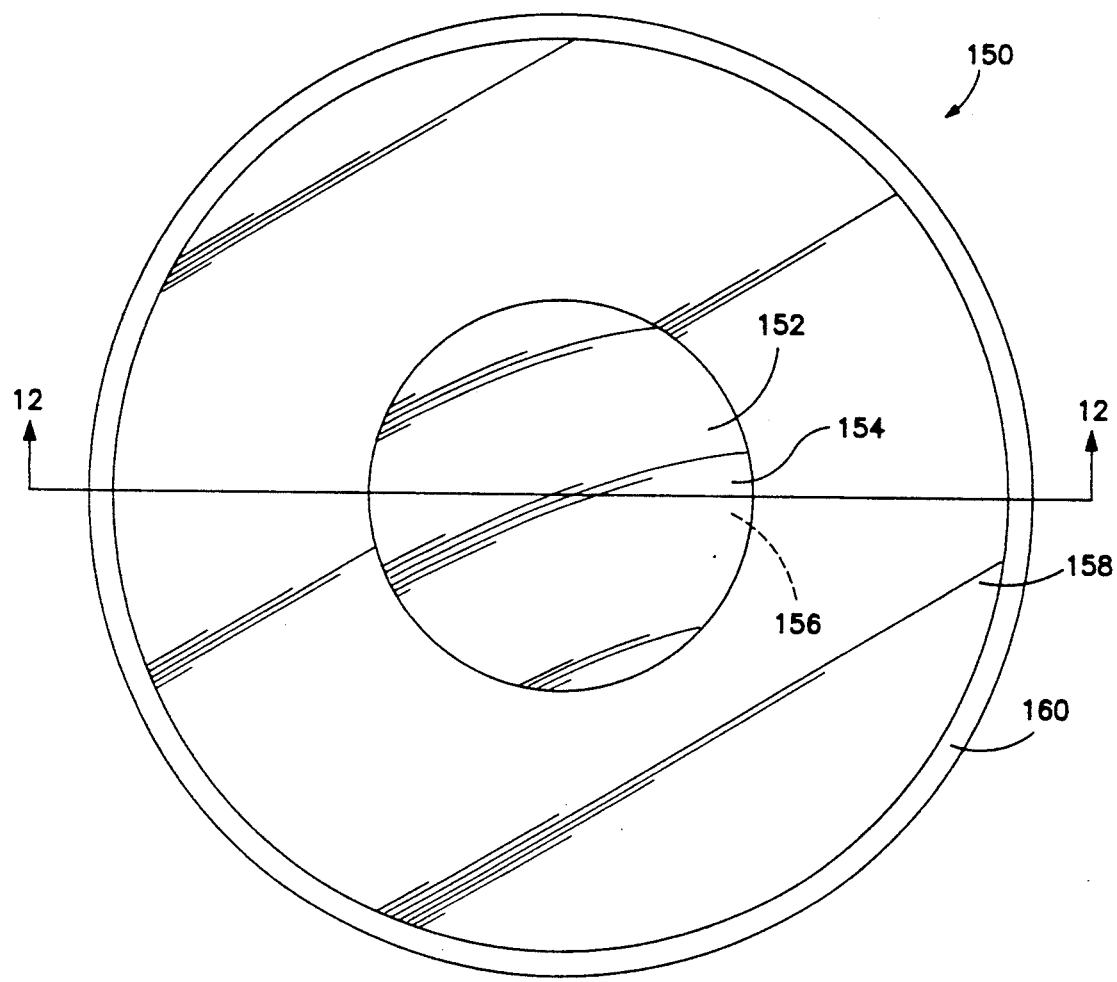
FIG. 11 illustrates a fourth alternative embodiment of an intraocular lens with an unembedded stiffener member; and, FIG. 12 illustrates a cross-sectional view along lines 12—12 of FIG. 11.

FIG. 11 illustrates a fourth alternative embodiment of an intraocular lens 150 including a central optic 152 with an anterior surface 154, a posterior surface 156, a flexible skirt member 158 about the central optic 152, and flexible polymer arcular stiffener member 160 secured about the peripheral edge of the flexible skirt member 158. The arcular stiffener member 160, while not embedded in the edge of the flexible skirt member 158, functions in the same fashion and manner as its corresponding stiffener members described in the previously described figures.

In the alternative, a flexible polymer arcular stiffener member similar to the illustrated arcular stiffener member 160 can also be suitably secured on the top or bottom surface of the flexible skirt member 158 adjacent to its peripheral edge or can be located at any appropriate distance inward of the peripheral edge either on the top or bottom surface. The similar arcular stiffener member can also be molded into the flexible skirt member 158 at any suitable distance from its peripheral edge.

Figure 12:
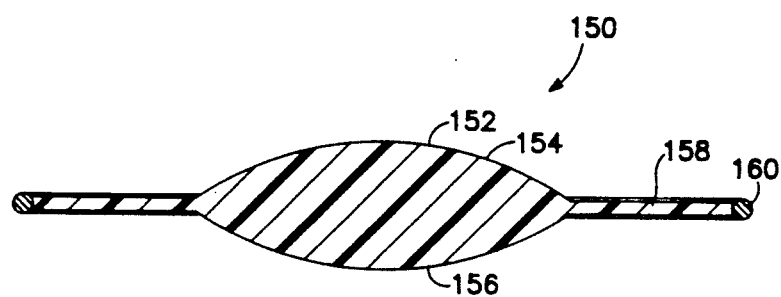

FIG. 12 illustrates a cross-sectional view along lines 12—12 of FIG. 11 where all numerals correspond to those elements previously described.

Alternatively, the skirt and support members may be angled or curved ("vaulted") forward or backward out of the plane of the lens optics.

Alternatively, the stiffener 160 may be secured on the surface of the flexible skirt 158 at or suitably near its peripheral edge, or at any appropriate intermediate distance.

Various modifications can be made to the present invention without departing from the apparent scope hereof.

I claim:

1. An intraocular lens comprising:
   a. an optic;
   b. a substantially circular continuous flexible skirt surrounding said optic and secured to said optic so as to form a predetermined geometrical shape, said skirt terminating in an arcuate edge having a cross section thicker than the cross section of said skirt; and,
   c. a reinforcing element embedded within said arcuate edge about its entire perimeter for reinforcing said skirt with respect to said optic and providing flexibility for folding through a small incision of an eye and having memory to return said skirt to the original predetermined geometrical shape after being folded.

2. The intraocular lens of claim 1 wherein said skirt is opaque.

3. The intraocular lens of claim 1 wherein said optic is flexible.

* * * * *